United States Patent
Badiey et al.

(10) Patent No.: US 8,760,970 B2
(45) Date of Patent: Jun. 24, 2014

(54) METHOD FOR DETECTION OF A PLUME OF A FIRST FLUID WITHIN A SECOND FLUID

(75) Inventors: Mohsen Badiey, Newark, DE (US); Boris G. Katsnelson, Voronezh (RU); James F. Lynch, East Falmouth, MA (US)

(73) Assignee: University of Delaware, Newark, DE (US)

( * ) Notice: Subject to any disclaimer, the term of this patent is extended or adjusted under 35 U.S.C. 154(b) by 339 days.

(21) Appl. No.: 13/273,852

(22) Filed: Oct. 14, 2011

(65) Prior Publication Data

US 2012/0195168 A1    Aug. 2, 2012

Related U.S. Application Data

(60) Provisional application No. 61/393,509, filed on Oct. 15, 2010.

(51) Int. Cl.
*G01S 15/06* (2006.01)
(52) U.S. Cl.
USPC ........................................................ 367/124
(58) Field of Classification Search
CPC ................... G01N 29/032; G01N 2291/0222; G01N 2291/103; G01S 15/003; G01S 15/58
USPC ........................................................ 367/124
See application file for complete search history.

(56) References Cited

U.S. PATENT DOCUMENTS

| 2006/0215489 A1 | 9/2006 | Solheim et al. |
| 2008/0080313 A1 | 4/2008 | Brumley et al. |
| 2008/0291082 A1 | 11/2008 | Kemkemian |
| 2012/0195168 A1* | 8/2012 | Badiey et al. .................. 367/93 |
| 2012/0197604 A1* | 8/2012 | Badiey et al. .................... 703/2 |

FOREIGN PATENT DOCUMENTS

WO    WO 2012051520 A3 *  4/2012    .............. G01S 15/06

OTHER PUBLICATIONS

Badiey, Mohsen, "Measurement and Modeling of Three-Dimensional Sound Intensity Variations Due to Shallow-Water Internal Waves", J. Acoust. Soc. Am. 117(2), (Feb. 2005) 613-625.
Badiey, Mohsen, "Frequency Dependence and Intensity Fluctuations Due to Shallow Water Internal Waves", J. Acoust. Soc. Am. 122(2), (Aug. 2007) 747-760.
Badiey, Mohsen, "Acoustic Multipath Arrivals in the Horizontal Plane Due to Approaching Nonlinear Internal Waves", J. Acoust. Soc. Am. 129(4), (Apr. 2011) 7 pgs.

(Continued)

*Primary Examiner* — Daniel Pihulic
(74) *Attorney, Agent, or Firm* — RatnerPrestia

(57) ABSTRACT

Methods and systems for detecting a plume of a first fluid in a second fluid using an acoustic wave are provided, where the first fluid has a different acoustic index of refraction than the second fluid. A horizontal array having a plurality of receiving elements receives an acoustic signal propagated through the second fluid and at least one refracted signal refracted by the first fluid. The acoustic signal and the at least one refracted signal form a received signal. An interference pattern is detected from the received signal over the plurality of receiving elements. The interference pattern is due to interference between the acoustic signal and the at least one refracted signal. A horizontal angle of refraction is determined between the acoustic signal and the at least one refracted signal from the interference pattern. The horizontal angle of refraction is indicative of a physical characteristic of the first fluid.

18 Claims, 7 Drawing Sheets

(56) References Cited

OTHER PUBLICATIONS

Badiey, M., "Temporal and Azimuthal Dependence of Sound Propagation in Shallow Water with Internal Waves", IEEE Journal of Oceanic Engineering, vol. 27, No. 1, (Jan. 2002) 117-129.

Burridge, Robert, "Horizontal Rays and Vertical Modes", Wave Propagation and Underwater Acoustics, Lecture Notes in Physics, vol. 70, (1997) 86-152.

Doolittle, R., "Experimental Confirmation of Horizontal Refraction of CW Acoustic Radiation from a Point Source in a Wedge-Shaped Ocean Environment", J. Acoust. Soc. Am. 83(6), (Jun. 1988) 2117-2125.

Headrick, Robert H., "Acoustic Normal Mode Fluctuation Statistics in the 1995 SWARM Internal Wave Scattering Experiment", J. Acoust. Soc. Am. 107(1), (Jan. 2000) 201-220.

Jiang, Yong-Min, "Short Range Travel Time Geoacoustic Inversion with Vertical Line Array", J. Acoust. Soc. Am., vol. 124, No. 3, Pt. 2, (Sep. 2008) 6 pgs.

Katsnel'son, B. G., "Space-Frequency Distribution of Sound Field Intensity in the Vicinity of the Temperature Front in Shallow Water", Acoustical Physics, vol. 53, No. 5, (2007) 611-617.

Katsnel'son, B. G., "Low-Frequency Horizontal Acoustic Refraction Caused by Internal Wave Solitons in a Shallow Sea", Acoustical Physics, vol. 46, No. 6, (2000) 684-691.

Lagerloef, Gary S.E., "Empirical Orthogonal Function Analysis of Advanced Very High Resolution Radiometer Surface Temperature Patterns in Santa Barbara Channel", Journal of Geophysical Research, vol. 93, No. C6, Jun. 15, 1988, pp. 6863-6873, 6979.

Lynch, James, "Overview of Shallow Water 2006 JASA EL Special Issue Papers", J. Acoust. Soc. Am., vol. 124, No. 3, Pt. 2, (Sep. 2008) 3 pgs.

Lynch, James F., "Consideration of Fine-Scale Coastal Oceanography and 3-D Acoustics Effects for the ESME Sound Exposure Model", IEEE Journal of Oceanic Engineering, vol. 31, No. 1, (Jan. 2006) 33-48.

Newhall, Arthur E., "Acoustic and Oceanographic Observations and Configuration Information for the WHOI Moorings from the SW06 Experiment", Woods Hole Oceanographic Institution, (May 2007) 119 pgs.

Weinberg, Henry, "Horizontal Ray Theory for Ocean Acoustics", J. Acoust. Soc. Am., vol. 55, No. 1, (Jan. 1974) 63-79.

Badiey, M., "Horizontal Reflection of a Low-Frequency Sound Signal From a Moving Nonlinear Internal Wave Front", J. Acoust. Soc. Am., vol. 127, No. 3, Pt. 2, Mar. 2010, 1 pg.

International Search Report for International Application No. PCT/US2011/056339, dated Apr. 10, 2012.

\* cited by examiner

METHOD FOR DETECTION OF A PLUME OF A FIRST FLUID WITHIN A SECOND FLUID

CROSS REFERENCE TO RELATED APPLICATIONS

This application claims priority to U.S. Provisional Application Ser. No. 61/393,509, entitled "METHOD FOR DETECTION OF A PLUME OF FIRST FLUID WITHIN A SECOND FLUID," filed Oct. 15, 2010, incorporated fully herein by reference.

STATEMENT REGARDING FEDERALLY SPONSORED RESEARCH

The present invention was supported in part by Grant Number N000141010396 from the Office of Naval Research. The United States Government may have certain rights to the invention.

FIELD OF THE INVENTION

The present invention relates to the field of internal wave detection and, more particularly, to methods and systems for detecting a plume of a first fluid within a second fluid based on detection of an interference pattern by an array of receiving elements in the second fluid.

BACKGROUND OF THE INVENTION

Shallow water environments are typically variable. For example, acoustic signals can be refracted (or reflected) from various boundaries including the sea surface and the sea bottom. Acoustic signals can also be refracted (reflected) within the water column itself, such as from temperature fronts and internal waves. Internal waves, for example, can produce large fluctuations on shallow water signals, both in amplitude and phase. These fluctuations may affect underwater array processing results, such as for source localization and inverse problem (medium) studies.

In general, internal waves are gravity waves that may oscillate within a fluid medium. (Nonlinear solitary internal waves are typically referred to as solitons). For example, an internal wave may propagate along the boundary between low and high density water regions. Internal waves may propagate vertically as well as horizontally.

It is desirable to detect fluctuations, such as internal waves, in the water column.

SUMMARY OF THE INVENTION

The present invention is embodied in methods for detecting a plume of a first fluid within a second fluid, where the first fluid has a different index of refraction than the second fluid. The method includes the step of receiving, by a horizontal array having a plurality of receiving elements, an acoustic signal propagated through the second fluid and at least one refracted signal refracted by the first fluid, where a combination of the acoustic signal and the at least one refracted signal form a received signal. The method also includes detecting an interference pattern from the received signal over the plurality of receiving elements. The interference pattern is due to interference between the acoustic signal and the at least one refracted signal. The method also includes determining a horizontal angle of refraction between the acoustic signal and the at least one refracted signal from the interference pattern, where the horizontal angle of refraction is indicative of a physical characteristic of the first fluid.

The present invention is further embodied in systems for detecting a plume of a first fluid within a second fluid, where the first fluid has a different index of refraction than the second fluid. The system includes a horizontal array having a plurality of receiving elements and a processor. The horizontal array receives an acoustic signal propagated through the second fluid and at least one refracted signal refracted by the first fluid, where a combination of the acoustic signal and the at least one refracted signal forming a received signal. The processor is configured to: detect an interference pattern from the received signal over the plurality of receiving elements, where the interference pattern is due to interference between the acoustic signal and the at least one refracted signal, and determine a horizontal angle of refraction between the acoustic signal and the at least one refracted signal from the interference pattern. The horizontal angle of refraction is indicative of a physical characteristic of the first fluid.

Systems and methods of the present invention may be used, for example, by the navy, for oil exploration, for oceanography, etc.

BRIEF DESCRIPTION OF THE DRAWINGS

The invention may be understood from the following detailed description when read in connection with the accompanying drawing. It is emphasized that, according to common practice, various features of the drawing may not be drawn to scale. On the contrary, the dimensions of the various features may be arbitrarily expanded or reduced for clarity. Moreover, in the drawing, common numerical references are used to represent like features. Included in the drawing are the following figures.

DETAILED DESCRIPTION OF THE INVENTION

Figure 1:
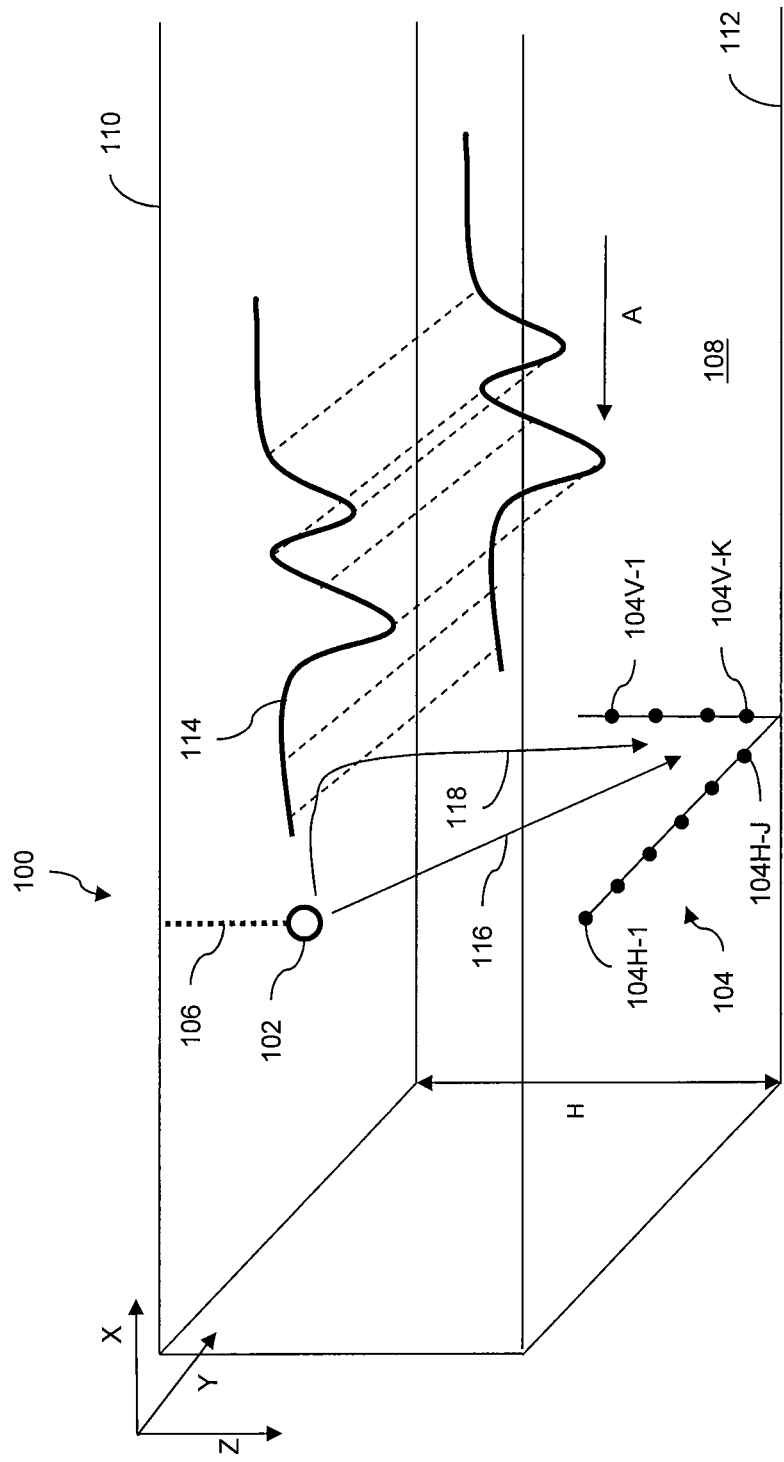
FIG. 1 is a perspective view diagram illustrating components of an exemplary system for detecting a plume of a fluid within an underwater channel, according to aspects of the present invention.

Aspects of the present invention relate to methods and systems for the detection of a plume of a first fluid horizontally moving within a second fluid (such as a water column). The first fluid may have an acoustic index of refraction different from an acoustic index of refraction of the second fluid. According to an exemplary method, an acoustic signal propagated through the second fluid and at least one refracted signal may be received by a horizontal array having a plurality of receiving elements. The at least one refracted signal may be the acoustic signal refracted by the plume. An interference pattern may be detected from interference between the acoustic signal and the at least one refracted signal as received by the horizontal array as a function of receiving element position. A horizontal angle of refraction between the acoustic signal and the at least one refracted signal may be determined from the interference pattern. The horizontal angle of refraction may be used to estimate one or more physical characteristics of the plume, such as salinity, viscosity, temperature, etc. The interference pattern may also be used to determine a velocity of the plume.

The plume may include an internal wave (including non-linear internal waves), a temperature front, or any oceanographic feature that may be moving inside the water column in a horizontal direction (i.e., the X-Y plane). In general, the first fluid represents any fluid having an acoustic index of refraction different from the second fluid. The second fluid may be a shallow water region, an underwater channel or a water column.

According to an exemplary method of the present invention, a small horizontal angle of refraction of acoustic waves in shallow water regions may be measured. The range of the small angle may be about less than 10 degrees. For example, internal waves may cause the acoustic signal (also referred to herein as acoustic rays) to refract. An internal wave that approaches a sound source-receiver path (also referred to herein as an acoustic track) may cause interference to occur between refracted rays in the horizontal direction. The interference may be measured from the envelope of the received signal, as well as for individual waveguide modes (by mode filtering). For example, some waveguide modes may be more sensitive to interferences than other waveguide modes.

Interferometry techniques are known in optics. In particular, the Lloyd's mirror effect is known in optics, and relates to the detection of interfering rays due to an approaching layer having different refraction properties. According to aspects of the present invention, acoustic ray interference in the horizontal direction may be determined, due to a moving plume with a different index of refraction from the water column.

Conventional beamforming techniques may be used to measure the angle of refraction. However, conventional beamforming techniques typically require a very large array (for example, several kilometers in length). In contrast, exemplary embodiments of the present invention use interferometry techniques, and are able to determine the angle of refraction using a horizontal array of only a few hundred meters or an L-shaped array (having a vertical component and a horizontal component). According to an exemplary embodiment, an L-shaped array having a horizontal array component of 300 m and a vertical array component of 80 meters may be used to determine the angle of refraction.

According to aspects of the invention, the acoustic signals used are generally low frequency signals, less than about 500 Hz, more preferably between about 100 Hz to 500 Hz. For shallow water channels (e.g., with a depth less than or equal to about 200 m), low frequency acoustic signals have small attenuation in comparison with signals at mid and high frequencies. For example, an attenuation coefficient of low frequency signals in a shallow water waveguide, under realistic conditions may be about 0.05-0.1 dB/km. At the same time, for a frequency of about 10 kHz, the attenuation coefficient may be more than 1 dB/km (in other words 10-20 times greater than for low frequencies). A similar ratio occurs with respect to propagation distance for low frequencies as compared with mid and higher frequencies.

Referring to FIG. 1, an exemplary plume detection system, designated generally as system 100, is described. System 100 may include source 102 and receiver array 104 in underwater channel 108 (i.e., a second fluid). Underwater channel 108 has a depth H between top surface 110 and bottom surface 112. Source 102 and receiver array 104 may be located at fixed and precisely known positions around an area of operation of underwater channel 112. Although underwater channel 108 is described herein, it is understood that underwater channel 112 may represent any water column.

System 100 may optionally include one or more vertical chains of thermistors, for example, thermistor string 106. Thermistor string 106 may be connected to source 102 or may be positioned in an operating area proximate source 102 and receiver array 104. As described further below, thermistor string 102 may be used to measure a sound speed profile associated with underwater channel 108 in the operating area.

Receiver array 104 may include horizontal array 104H having a plurality of receiving elements 104H-1, . . . , 104H-J (e.g., hydrophones) disposed on bottom surface 110 of underwater channel 108. Receiver array 104 may also include vertical array 104V having a plurality of receiving elements 104V-1, . . . , 104V-K (e.g., hydrophones) disposed along a depth (Z axis) of underwater channel 108. K and J are integers and may be greater than or equal to 2, where K may be equal or may not be equal to J. Accordingly, in FIG. 1, receiver array 104 represents an L-shaped array. According to another embodiment, receiver array 104 may include a horizontal array (i.e., horizontal array 104H). In general, receiver array 104 desirably includes at least horizontal array 104H.

Underwater channel 108 may include plume 114 moving in a horizontal direction (i.e., in the X-Y plane), designated generally by arrow A, toward system 100. Plume 114 is illustrated as an internal wavefront, but may include any fluid (i.e., a second fluid) having a different (acoustic) refractive index from underwater channel 108. Plume 114 may an acoustic track (between source 102 and receiver array 104) in a small horizontal angle (i.e., a small angle between the acoustic track and the wave front of plume 114). The angle may be less than about 10°.

Source 102 may be configured to transmit acoustic signal 116 (also referred to herein as direct signal 116) through underwater channel 108. Acoustic signal 116 may be of low frequency (i.e., having a low frequency component (e.g., 100-500 Hz)). Acoustic signal 116 may be received by receiver array 104 and may be used to detect an interference pattern caused by plume 114 (described further below).

Acoustic signal 116 transmitted by source 102 may be a narrowband or a broadband signal. Acoustic signal 116 may include a plurality of pulses repeated periodically, such as a linear frequency modulated (LFM) signal (e.g., a chirp) or may include a continuous signal, such as a pseudorandom binary sequence (e.g., a maximum length sequence (MLS)).

In general, system 100 of the present invention may use low frequency acoustic signals in shallow water areas (such as coastal areas) where propagation of sound signals has a waveguide character. Based on a measurement (or estimate) of the sound speed profile with respect to a depth of the channel, a waveguide propagation model of the channel may be established and modal group velocities of waveguide modes may be determined. In an exemplary embodiment, the interference pattern may be detected based on at least one waveguide mode.

In general, the sound speed profile may be a function of temperature, salinity and hydrostatic pressure. For a typical shallow water channel 108, hydrostatic pressure and salinity may provide a small contribution. Accordingly, the sound speed profile may be determined by the temperature of channel 108 as a function of depth. Thus, on the basis of temperature, the modal structure of the sound field in the operating area of underwater channel 108 may be determined and used to calculate the modal group velocities of the separate waveguide modes.

The sound speed profile may be estimated based on archival records for the region. For example, the records may provide an indication of the sound speed profile at different times of the day as well as for different seasons. Alternatively, or in combination, the sound speed profile may be measured within the operating region, for example by a plurality of thermistors (such as thermistor string 106). If the shallow water channel 108 is relatively time-invariant, for example, the archival records may provide an adequate estimate of the sound speed profile. If the shallow water channel 108 is relatively variable with time, measurements of the sound speed profile as a function of depth may be performed, for example, every couple of minutes. Accordingly, an adequate model of a variable medium and calculations of group velocities of separate waveguide modes may be updated every couple of minutes.

In operation, as plume approaches system 100, acoustic signal 116 is refracted by plume 114, forming refracted signal 118. Direct signal 116 and refracted signal 118 represent horizontal ray paths (shown further in FIG. 4) (in the X-Y plane). Interference between direct signal 116 and refracted signal 118 may produce an interference pattern which may be detected by receiver array 104 (both by horizontal array 104H and vertical array 104V). Both modal contents and horizontal ray contents of acoustic wave propagation may be affected by interaction with plume 114, causing the received signal at receiving array 104 to have a fluctuating intensity.

Figure 2:
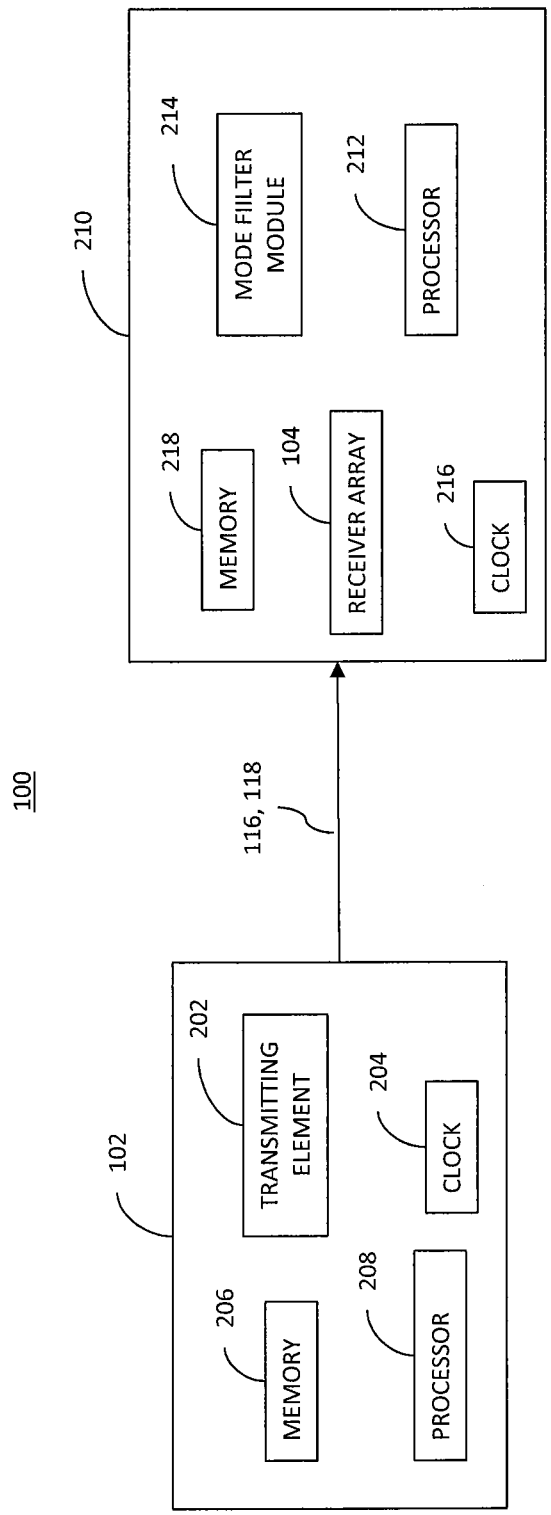
FIG. 2 is functional block diagram of components of the exemplary system shown in FIG. 1, according to aspects of the present invention.

Referring next to FIG. 2, a function block diagram of system 100 is shown. System 100 may include source 102 and receiver module 210, where receiver module 210 may receive direct signal 116 and one or more refracted signals 118.

Source 102 may include transmitting element 202 (e.g., a transducer) for transmitting acoustic signal 116 and clock 204. Source 102 may also include one or more of memory 206 and processor 208. Memory 206 may store parameters for generating acoustic signal 116. Processor 208 may, for example, control transmission of acoustic signal 116 from transmitting element 202 at predetermined transmission times, responsive to clock 204. Although transmitting element 202 is shown, transmitting element 202 may include a transceiver, for transmitting acoustic signal 116 and for receiving further signals.

Receiver module 210 may include receiver array 104 for receiving acoustic signal 116 and one or more refracted signals 118, processor 212 for detecting plume 114 (FIG. 1) and memory 218. Receiver module 210 may also include clock 216 which may be synchronized with clock 204 of source 102. Memory 218 may store, for example, sound speed profiles, one or more modal group velocities, the predetermined transmission times of source 102, interference patterns and/or received signals (i.e., from direct and refracted signals 116, 118). Although not shown, receiver array 104 may optionally include a transceiver function, for transmitting an further acoustic signal and for receiving acoustic signal 116 and refracted signal(s) 118.

Receiver module 210 may also include mode filter module 214 for distinguishing mode separation upon receipt of the direct and refracted signals 116, 118. It may be desirable to distinguish the mode separation, because the interference pattern may be more prominent for particular modes. The separation of waveguide modes may be performed using standard methods of signal processing (such as via bandpass or notch filters of mode filter module 214) and separation of modal pulses in time or using radiation of separate modes.

Receiver module 210 may determine a sound speed profile of the operating region (for example by thermistor string 106 (FIG. 1)) or may receive the sound speed profile via a remote observer, where the sound speed profile may be used to determine the modal group velocities, described further below.

It is understood that receiver array 104 may be directly connected to processor 208 (and mode filter module 214) or receiver array 104 may be remotely connected. Interference pattern results and/or received signals may also be transmitted to a remote location (not shown) for further analysis and/or storage.

Each processor 208, 212 may include, for example, a logic circuit, a digital signal processor or a microprocessor. Suitable transmitting element, 202, receiver array 104, clocks 204, 216, memories 206, 218, processors 208, 212 and mode filter module 214 may be understood by the skilled person from the description herein.

Figure 3:
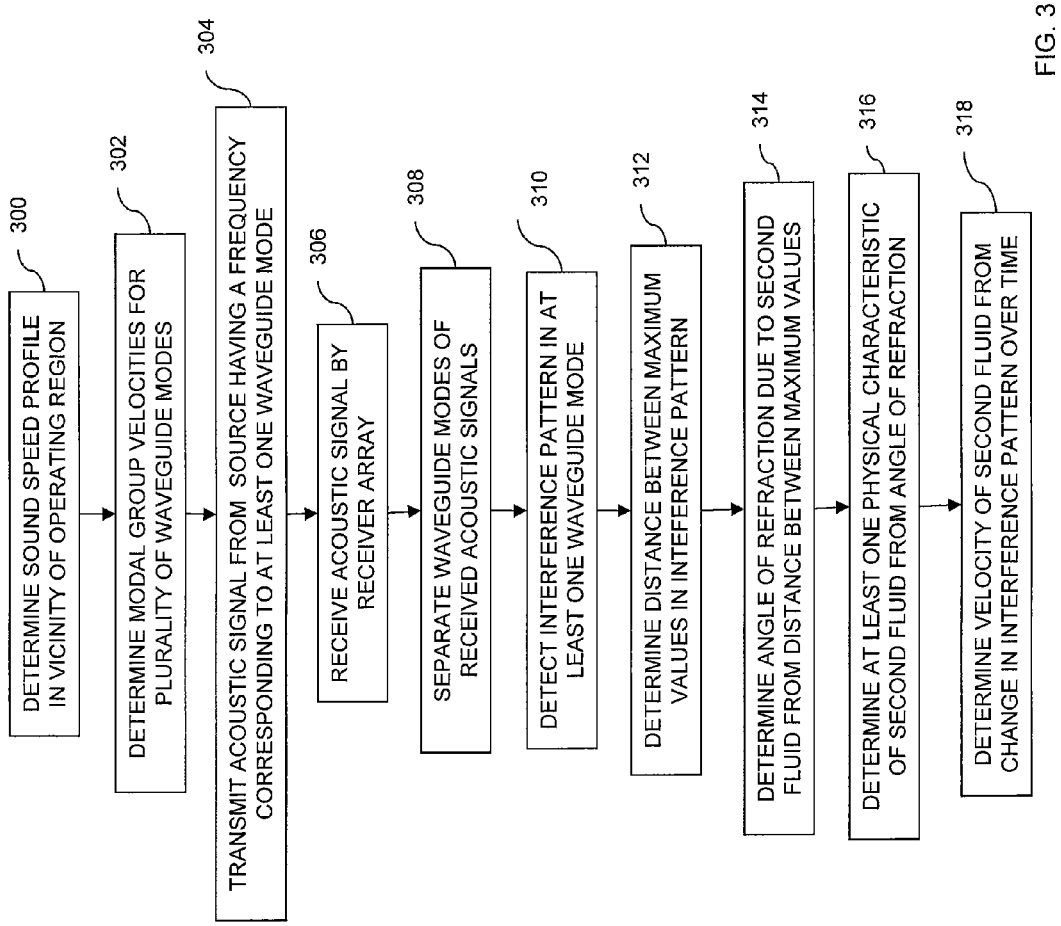
FIG. 3 is a flow chart diagram illustrating an exemplary method for detecting a plume of fluid within an underwater channel, according to an aspect of the present invention.

Referring next to FIG. 3, an exemplary method for detecting a plume of fluid (i.e., a second fluid) in an underwater channel (i.e., a first fluid) is shown. The steps illustrated in FIG. 3 represent an example embodiment of the present invention. It is understood that certain steps may be performed in an order different from what is shown.

At step 300, a sound speed profile may be determined in the vicinity of the operating region of system 100 (FIG. 1). For example, sound speed profiles may be estimated (as described above) or measured (such as via thermistor string 106 shown in FIG. 1) via processor 212 (FIG. 2) of corresponding receiver module 210. The sound speed profile may be stored in memory 218 (FIG. 2) of receiver module 210.

At step 302, a modal group velocity may be determined for a plurality of waveguide modes, for example, by processor 212 (FIG. 2) of receiver module 210. The modal group velocity may be determined from the sound speed profile (step 300).

At step 304, an acoustic signal (for example, acoustic signal 116 shown in FIG. 1) may be transmitted from sources 102 (for example by transmitting element 202 (FIG. 2). The acoustic signal may include a frequency corresponding to at least one waveguide mode associated with underwater channel 108 (FIG. 1). Acoustic signal 116 (FIG. 1) may be transmitted from source 102 at predetermined transmission times.

At step 306, the acoustic signal (transmitted by source 102 (FIG. 1)) may be received by receiving elements 104H (and optionally receiving elements 104V) of receiver array 104. At optional step 308, waveguide modes of the received acoustic signal may be separated, for example by mode filter module 214 (FIG. 2) of receiver module 210. The received signal may include, for example, direct signal 116 (FIG. 1) as well as refracted signal 118, depending upon a position of plume 114 in underwater channel 108 relative to system 100.

At step 310, an interference pattern may be detected in at least one waveguide mode, for example, by processor 212 (FIG. 2) of receiver module 210. The interference pattern may be formed due to interference between direct signal 116 (FIG.

1) and at least one refracted signal 118 as received by individual receiving elements 104H-1, . . . , 104H-J (and optionally receiving elements 104V-1, . . . , 104V-K) of receiver array 104. The interference pattern may be detected after mode separation (step 308) or from an envelope of the received signal at receiver array 104.

At step 312, a distance between maximum values in the interference pattern may be determined, for example, by processor 212 (FIG. 2) of receiver module 210. At step 314, an angle of refraction may be determined (due to plume 114 (FIG. 1)) from the distance (determined at step 312).

At step 316, at least one physical characteristic of plume 114 (FIG. 1) may be determined from the angle of refraction (determined at step 312). For example, a salinity, a viscosity, a temperature, etc., of plume 114 (FIG. 1). At step 318, a velocity of plume 114 (FIG. 1) may be determined from changes in the interference pattern over a period of time. For example, the position of the maximum values in the interference pattern may be observed over the time period to determine the velocity.

Figure 4:
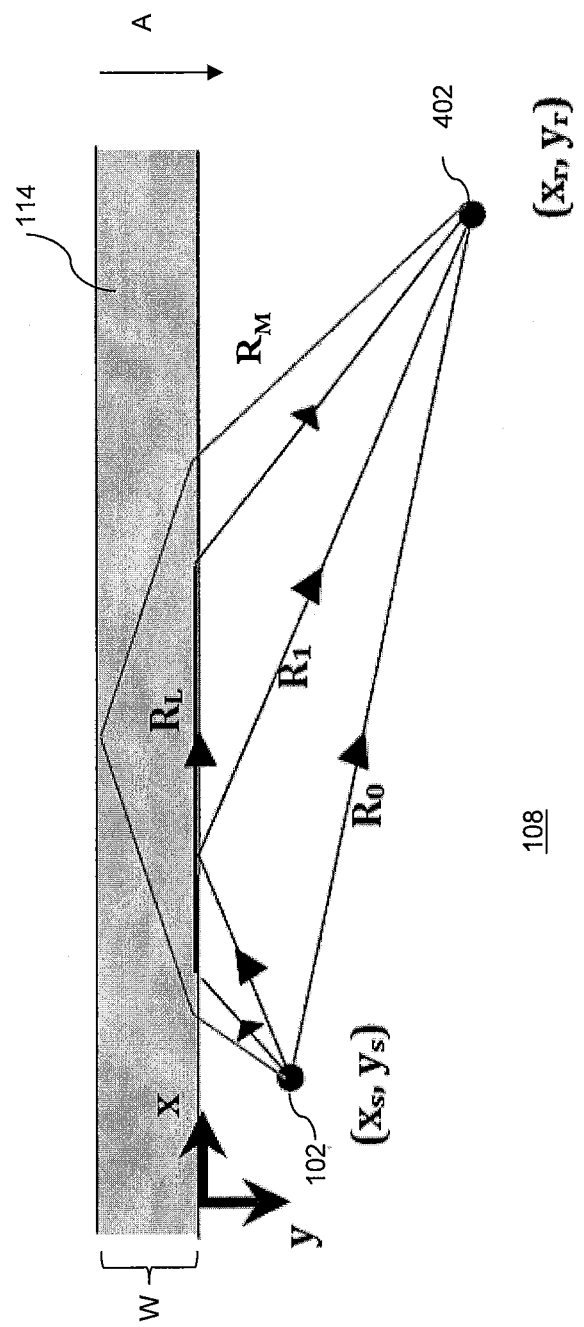
FIG. 4 is a top plan view diagram of an exemplary underwater channel having a plume of fluid moving in the horizontal plane, illustrating the behavior of acoustic rays in a vicinity of the plume, according to an aspect of the present invention.

Referring to FIG. 4, a top plan view diagram (i.e., in the X-Y plane) is shown of underwater channel 108 having plume 114 (having width W) propagating (with an approaching speed) in direction A toward source 102 and receiver point 402. Source 102 is at position $(x_s, y_s)$. Receiver point 402 is at position $(x_r, y_r)$. FIG. 4 illustrates the behavior of acoustic rays $R_0$, $R_1$, $R_L$ and $R_M$ in a vicinity of plume 114. Acoustic ray $R_0$ represents the direct ray propagated through underwater channel 108 (without being influenced by plume 114). Acoustic rays $R_1$ and $R_L$ represent acoustic rays that are reflected at a boundary between plume 114 and underwater channel 108. Acoustic ray $R_M$ represents an acoustic ray that is refracted through plume 114 and directed out plume 114 to underwater channel 108.

If horizontal array 104H (FIG. 1) is positioned at receiver point 402, providing an aperture for the received acoustic wavefront, then the angle between the direct ray $R_0$ and the reflected and refracted paths $R_1$, $R_L$ and $R_M$ may be determined. The angle may be used to obtain information regarding the approaching plume 114. For example, plume 114 may be a temperature front or a salinity front which may change the index of refraction of plume 114. In addition to temperature and salinity, other factors may change the (acoustic) index of refraction, such as the viscosity of plume 114. An interference pattern due to interference between rays $R_0$ $R_1$, $R_L$ and $R_M$ at receiver point 402 may be detectable by a horizontal array 104H (FIG. 1) or L-shaped array 104.

Figure 5B:
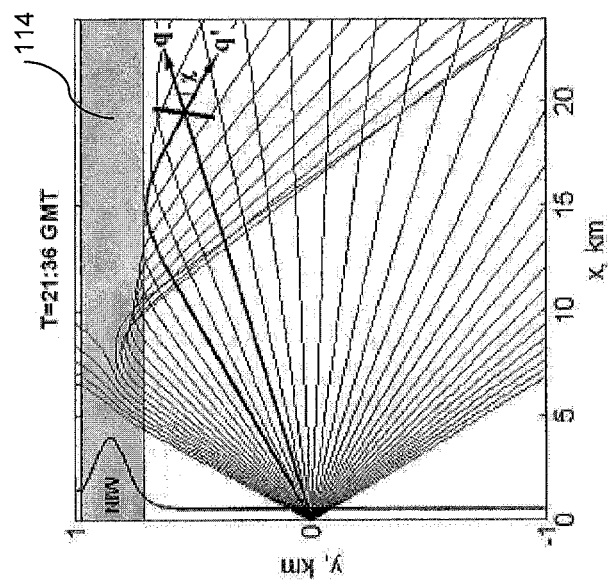
FIGS. 5A and 5B are top plan view diagrams of acoustic rays in an underwater channel as a function of distance between a source and a receiver array without a plume of fluid and with a plume of fluid, respectively, according to an aspect of the present invention.
Figure 5A:
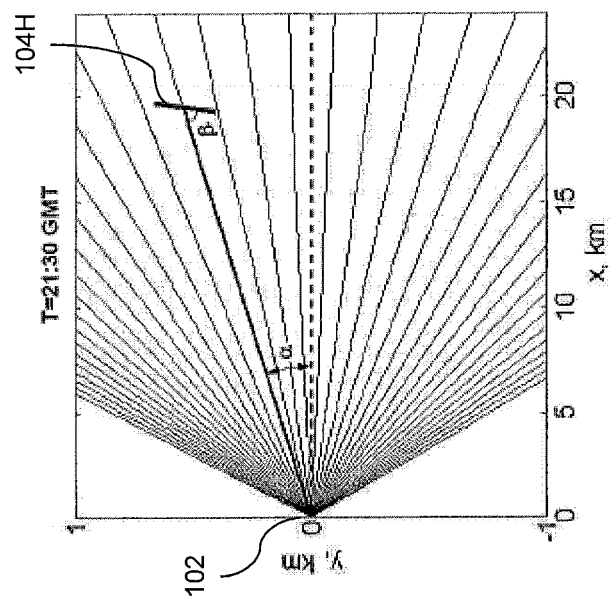

Referring to FIGS. 5A and 5B, top plan view diagrams (i.e., in the X-Y plane) are shown of acoustic rays in an underwater channel as a function of distance between source 102 and horizontal receiver array 104H. In particular, FIG. 5A represents the underwater channel without a plume of fluid. Thus, in FIG. 5A, receiver array 104 receives direct rays from source 102. FIG. 5B represents the underwater channel with a plume 114 of fluid. In FIG. 5A, receiver array 104H may receive direct rays from source 102 as well as refracted rays from plume 114.

With reference to FIGS. 5A and 5B, a detailed analysis of the interference effects by plume 114 of fluid moving in the horizontal plane and received by horizontal array 104H is given, based on the theory of vertical modes and horizontal rays.

Decomposition of vertical adiabatic modes due to a sound field with an amplitude $P(\vec{r}, z, t)$ from a point source with a spectrum $S(\omega)$ placed at $(x_s=0, y=0, z_s)$ or $(\vec{r}_s=0, z_s)$ is shown in eq. 1 as:

$$P(\vec{r},z,t)=2\int_0^\infty S(\omega)\Sigma_l P_l(\vec{r},\vec{r}_s)\Psi_l(\vec{r},z)e^{-i\omega t}d\omega \qquad (1)$$

where $\Psi_l$ are eigenfunctions (with $q_l$ being eigenvalues of a given shallow water waveguide), depending on $\vec{r}$, where l is an integer representing the mode number and where $\theta_l(\vec{r})$ represents a phase function. The complex modal amplitude $P_l(\vec{r},\vec{r}_s)$ is then $$P_l(\vec{r},\vec{r}_s)=A_l(\vec{r})e^{i\theta_l(\vec{r})} \qquad (2)$$

If there are several horizontal rays corresponding to one mode coming to one receiver point, a second sub-index should be indicated to denote a sum over horizontal rays in eq. (2). For the phase function $\theta_l(\vec{r})$, the standard eikonal equation of ray theory is obtained as:

$$(\nabla_r \theta_l)^2=(q_l^0)^2[1+\mu_l(\vec{r})] \qquad (3)$$

where $\mu_l(\vec{r})$ is a correction to an unperturbed refraction index in the absence of internal waves. The function $\mu_l(\vec{r})$ can be found, for example, using perturbation theory. For a situation where displacement of a thermocline layer on top of a soliton is directed down (for example, a positive direction of the Z axis), then this correction is negative ($\mu_l<0$) and provides deviation of refracted horizontal rays toward the acoustic track and formation of an area of multipath propagation (see FIG. 5B).

Depending on the position of plume 114 with respect to the acoustic track, the receiver array 104H falls either in an area of one-path propagation (FIG. 5A) or in the area of multi-path (or two-path) propagation where two rays (direct and refracted) reach receiver array 104H (FIG. 5B). Accordingly, an interference pattern should be observed in the multipath area, where the interference pattern may be formed by direct and refracted signals. At a later point in time (typically a few minutes for real conditions), receiver array 104H may fall into a shadow zone. Interference between the direct and the reflected wave fields is well known in optics and is called the Lloyd's mirror effect.

According to one embodiment, analysis of the received data at receiving array 104H may be carried out according to match filtered processing:

$$s(t)=F^{-1}[g(\omega)S^*(\omega)] \qquad (4)$$

where $F^{-1}[\cdot]$ is the inverse Fourier transform, $g(\omega)$ is the spectrum of received signal, $S^*(\omega)$ is the complex conjugate spectrum of radiated signal, s(t) is the amplitude of complex signal and $\omega 0$ represents the angular frequency. An envelope u(t) of the received signal s(t) may be determined as:

$$u(t)=\sqrt{s^2(t)+s_H^2(t)} \qquad (5)$$

where $s_H(t)=H[s(t)]$ is the Hilbert transform. An example envelope u(t) is shown in the FIGS. 7A-7C, described further below.

Parameters of the multipath area may be estimated, for example, such as the angle of horizontal refraction $\chi$ (shown in FIG. 5B) between direct and refracted signals and a velocity of plume 114. Typically, both direct and reflected signals coming to receiver array 104H consist of a few modes. For the estimation of the angle $\chi$, differences in the interference structure between modes may be neglected.

The inventors have determined that the intensity of the total field, as a sum of direct and refracted signals is (where amplitudes of signals are approximately equal) may be represented as:

$$I = \frac{|A|^2}{2} + \frac{|A'|^2}{2} + AA'\cos(q\rho\sin\chi\cos\beta - \varphi) \quad (6)$$

where A and A' are amplitudes of the direct and reflected signals, respectively; β is the angle between receiver array 104H and the acoustic track (shown in FIG. 5A); ρ (0<ρ<L) is the distance along HLA; and q is the modulus of vector $\vec{q}$.

The spatial period of beating along horizontal receiver array 104H may be represented as:

$$\Lambda = 2\pi/(q \sin\chi \cos\beta) \quad (7)$$

The relationship of eq. (7) allows estimation of angle χ, using the period of beating. In other words, a distance between adjacent maximums in the interference pattern may represent the period of beating. As an example, in an experiment over a particular time period, for a measured distance between adjacent maximums of about 100 m, with angle β of about 26° and a sound frequency of about 300 Hz; and angle χ of about 3-3.5° may be determined.

A phase shift φ along the reflected ray path in comparison with the direct ray path may also be estimated. Let the distance between source 102 and receiver array 104H be of length R, with the acoustical track being parallel to the wavefront of plume 114 at a distance $y_o$. If the direct and reflected rays are assumed to be straight lines, then $\varphi = 2y_o^2 q/R$.

While plume 114 is moving along the Y-axis, the interference pattern is also moving along receiver array 104H. Thus, the velocity plume 114 may be estimated from changes in the interference pattern. For example, if the velocity of a soliton is about 0.5-0.6 m/s, then the velocity v of interference maximums is about 2 v/(cos β), that gives for our conditions about 2.5 m/s.

An experiment (the Shallow Water 2006 experiment (SW06)) was performed on Aug. 17, 2006 for detecting a nonlinear internal wave (NIW) train, where the NIW train was moving toward the coast. Radar images of this train obtained during a few hours as well as records of thermistors placed approximately along the acoustic track, allow for a detailed description of this internal wave train. In the experiment, an acoustic track is between a NRL300 sound source (deployed at depth 72 m), transmitting linear frequency modulated (LFM) pulses with a central frequency 300 Hz and a bandwidth of 30 Hz, with a duration of 2.048 sec followed by 2 sec silence. Every transmission series contained 110 pulses with a total duration of 7.5 minutes followed by 30-minutes of silence.

A receiving L-shaped array (Shark array from Woods Hole Oceanographic Institution (WHOI)) was placed at the position (depth of about 79 m) at a distance of R of about 20 km from the sound source. A length of the horizontal part of the L-shaped array was about 465 m, containing 32 hydrophones. This array was placed horizontally on the sea floor with the angle of with the acoustic track (see FIGS. 5A and 5B). The direction of the NIW wavefront was almost parallel to acoustic track (estimated angle between the straight line NIW front and the acoustic track was about α of about 5°). Significant horizontal refraction was illustrated in the experiment.

Figure 6:
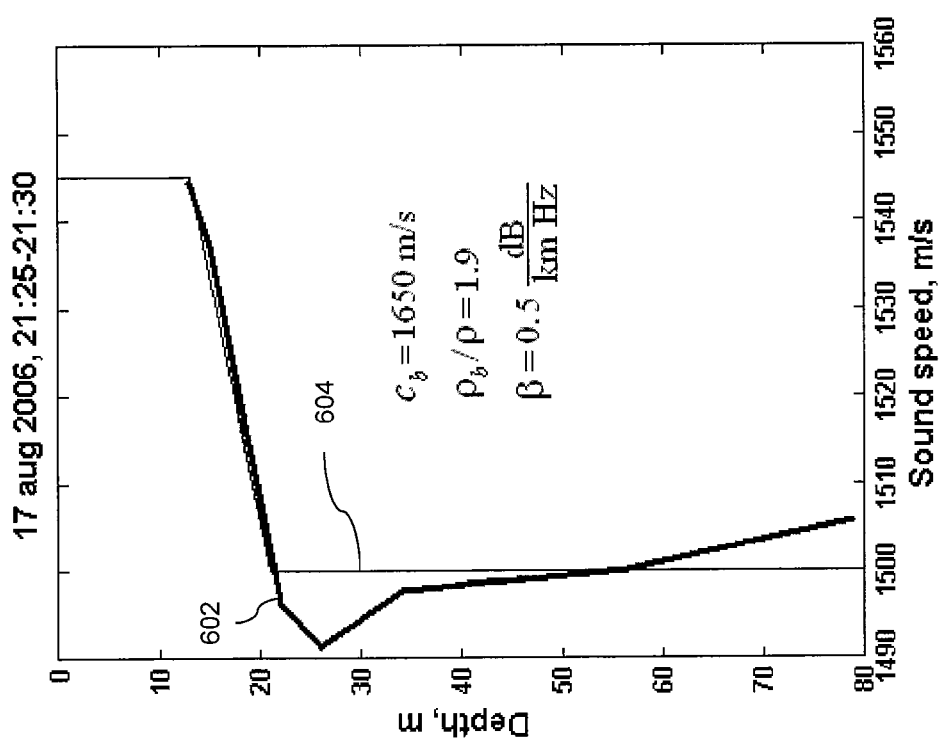
FIG. 6 is an example graph of depth as a function of sound speed illustrating measured and modeled sound speed profiles for an operating region of a source and an L-shaped receiver array, according to an aspect of the present invention.

FIG. 6 illustrates an average sound speed profile (curve 602) of the operating region and a model of the sound speed profile (curve 604). Parameters of the waveguide are shown in FIG. 6, where $c_b$ is the sound speed (1650 m/s), $\rho_b/\rho$ is seabed to water density ratio (1.9), and β is the acoustic attenuation coefficient $$\left(0.5 \frac{dB}{km\,Hz}\right).$$

Figure 7A:
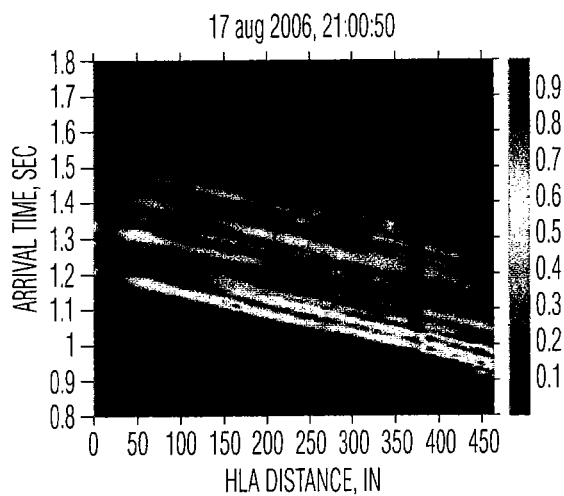
FIGS. 7A, 7B and 7C are example envelopes of acoustic energy received by an L-shaped array as a function of arrival time and distance along a horizontal portion of the L-shaped array, illustrating interference patterns due to a plume of fluid, according to an aspect of the present invention.
Figure 7B:
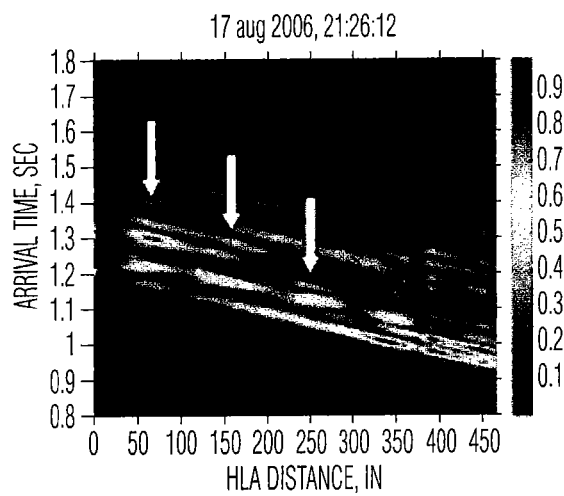
Figure 7C:
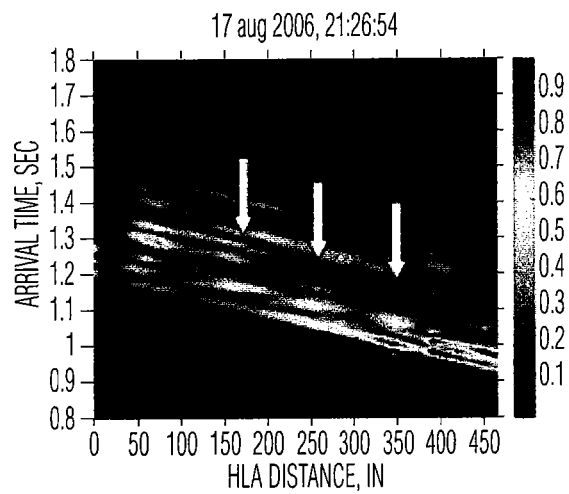

FIGS. 7A-7C are example envelopes of acoustic energy (determined as described above) received by the L-shaped array as a function of arrival time and distance along a horizontal portion of the L-shaped array, illustrating the occurrence and change of an interference pattern due to an NIW train, in which color corresponds to the intensity of the received signals as defined by the color key to the right of each figure. In FIG. 7A, the interference pattern is prior to the arrival of the NIW train. FIGS. 7B and 7C illustrate the change in the interference pattern after the NIW train interferes with the acoustic track. The arrows in FIGS. 7B and 7C indicate positions of maximum value of the interference structure, due to the interference between the direct and refracted rays.

FIGS. 7A-7C illustrate the arrival times of received pulses as a function of distance along the horizontal array. In FIG. 7A, there are a few inclined straight lines (about 5-8), each of which corresponds to the arrival of separate modes. Time intervals between adjacent arrivals (δt(0.03-0.05) s) correspond to differences in group velocities for the separate modes, where $\delta t \sim R(v_l - v_{l+1})/v_l^2$. Table 1 illustrates eigenvalues $q_l^0$, amplitudes $A_l$ and group velocities $v_l$ for the lowest 10 modes.

TABLE 1

| 1 | $q_l^0$, m$^{-1}$ | $A_l$ | $v_l$, m/s |
|---|---|---|---|
| 1 | 1.2558038682 | 0.48 | 1499.2 |
| 2 | 1.2533040982 | 1.00 | 1496.9 |
| 3 | 1.2491415460 | 0.82 | 1493.1 |
| 4 | 1.2433384404 | 0.40 | 1487.9 |
| 5 | 1.2359684931 | 0.12 | 1481.7 |
| 6 | 1.2272482585 | 0.02 | 1476.1 |
| 7 | 1.2178616043 | 0.02 | 1475.9 |
| 8 | 1.2093379600 | 0.05 | 1480.7 |
| 9 | 1.2004914808 | 0.02 | 1462.4 |
| 10 | 1.1892211190 | 0.01 | 1444.3 |

As shown in FIG. 7A, different modes have different intensities in accordance with the theoretical estimations shown in Table 1, where only about 4-5 modes have notable amplitudes. Inclination of these straight lines corresponds to the difference in arrival times for the first through the last hydrophones (due to the angle β=26° between the array and the acoustic track). This distance along acoustic track is about 420 m, which gives about 0.3 sec difference in arrival times.

In FIGS. 7B and 7C, the interference structure along the horizontal array is shown. Before geotime 21:34, it is comparatively stable (shown in the FIG. 7A). The scale of beating is determined by the difference between unperturbed eigenvalues $q_l^0$:

$$\Lambda_{lm} = 2\pi/(|q_l^0 - q_m^0|\cos\beta)$$

A minimal value of this scale is provided by beating between the first and fifth modes of about 350-370 m. This beating is of the order of length of HLA and no interference beating is indicated.

After 21:34 GMT (FIGS. 7A and 7B), there is a multipath and non stationary regime, with the appearance of an interference structure provided by two (or more) incoming signals which moves synchronously with motion of the NIW train.

In FIGS. 7A and 7B, two snapshots of the interference structure at the horizontal array when the receiver falls into multipath area are shown. FIGS. 7A and 7B illustrate the appearance of a moving interference structure (with maximums are shown by arrows) with spaced period of beating about 100 m. For the time 41 sec, the interference structure is shifted by 110 m, and therefore the velocity of the interference structure along horizontal array is about 2.7 m/s.

Although the invention has been described in terms of systems and methods for detecting a plume of a first fluid within a second fluid, it is contemplated that one or more steps and/or components may be implemented in software for use with microprocessors/general purpose computers (not shown). In this embodiment, one or more of the functions of the various components and/or steps described above may be implemented in software that controls a computer. The software may be embodied in non-transitory tangible computer readable media (such as, by way of non-limiting example, a magnetic disk, optical disk, hard drive, etc.) for execution by the computer.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method for detecting a plume of a first fluid within a second fluid, the first fluid having a different index of refraction than the second fluid, the method comprising the steps of:
   receiving, by a horizontal array having a plurality of receiving elements, an acoustic signal propagated through the second fluid and at least one refracted signal refracted by the first fluid, a combination of the acoustic signal and the at least one refracted signal forming a received signal;
   detecting an interference pattern from the received signal over the plurality of receiving elements, the interference pattern due to interference between the acoustic signal and the at least one refracted signal; and
   determining a horizontal angle of refraction between the acoustic signal and the at least one refracted signal from the interference pattern, wherein the horizontal angle of refraction is indicative of a physical characteristic of the first fluid.

2. The method according to claim 1, wherein the step of detecting the interference pattern includes:
   generating an envelope from the received signal over the plurality of receiving elements and over a period of time; and
   analyzing maximum values in the envelope to detect the interference pattern.

3. The method according to claim 1, wherein the step of detecting the interference pattern includes:
   filtering the received signal over the plurality of receiving elements to pass at least one waveguide mode associated with the second fluid; and
   analyzing maximum values in the filtered signal for the at least one waveguide mode to detect the interference pattern.

4. The method according to claim 1, wherein the step of determining the horizontal angle of refraction includes:
   detecting at least two adjacent maximum values in the interference pattern;
   determining a distance between the adjacent maximum values; and
   estimating the horizontal angle of refraction based on the distance.

5. The method according to claim 1, wherein the physical characteristic of the first fluid includes at least one of a salinity, a viscosity or a temperature.

6. The method according to claim 1, wherein the horizontal angle of refraction is less than about 10 degrees.

7. The method according to claim 1, wherein the plume of the first fluid includes at least one of an internal wave, a temperature front or an oceanographic feature.

8. The method according to claim 1, further comprising determining a velocity of the plume in a horizontal direction from the interference pattern.

9. The method according to claim 1, further comprising determining a phase shift between the acoustic signal and the at least one refracted signal.

10. The method according to claim 1, further including:
    receiving, by a vertical array having a further plurality of receiving elements, the received signal, wherein the interference pattern is detected from the plurality of receiving elements of the horizontal array and the further plurality of receiving elements from the vertical array.

11. The method according to claim 1, wherein the plume of the first fluid is moving within the second fluid in a horizontal direction.

12. A system for detecting a plume of a first fluid within a second fluid, the first fluid having a different index of refraction than the second fluid, the system comprising:
    a horizontal array having a plurality of receiving elements, the horizontal array receiving an acoustic signal propagated through the second fluid and at least one refracted signal refracted by the first fluid, a combination of the acoustic signal and the at least one refracted signal forming a received signal; and
    a processor configured to:
       detect an interference pattern from the received signal over the plurality of receiving elements, the interference pattern due to interference between the acoustic signal and the at least one refracted signal, and
       determine a horizontal angle of refraction between the acoustic signal and the at least one refracted signal from the interference pattern, wherein the horizontal angle of refraction is indicative of a physical characteristic of the first fluid.

13. The system according to claim 12, further comprising a vertical array having a further plurality of receiving elements, wherein the interference pattern is detected from the received signal over the plurality of receiving elements and the further plurality of receiving elements.

14. The system according to claim 12, wherein the processor is configured to detect at least two adjacent maximum values in the interference pattern and to determine a distance between the adjacent maximum values, wherein the horizontal angle of refraction is estimated based on the distance.

15. The system according to claim 12, wherein the physical characteristic of the first fluid includes at least one of a salinity, a viscosity or a temperature.

16. The system according to claim 12, wherein the plume of the first fluid includes at least one of an internal wave, a temperature front or an oceanographic feature.

17. The system according to claim 12, wherein the plume of the first fluid moves within the second fluid in a horizontal direction and the processor is configured to determine a velocity of the plume in the horizontal direction from the interference pattern.

18. The system according to claim 12, wherein the processor is configured to determine a phase shift between the acoustic signal and the at least one refracted signal.

* * * * *